United States Patent [19]

Farina et al.

[11] 4,337,339

[45] Jun. 29, 1982

[54] PROCESS FOR PREPARATION OF FOLIC ACID DERIVATIVES

[75] Inventors: Peter R. Farina, North Salem; James A. Grattan, Croton-on-Hudson, both of N.Y.

[73] Assignee: Baker Instruments Corp., Wilton, Conn.

[21] Appl. No.: 90,059

[22] Filed: Oct. 31, 1979

Related U.S. Application Data

[62] Division of Ser. No. 34,760, Apr. 30, 1979.

[51] Int. Cl.³ .................................................. C07D 475/04
[52] U.S. Cl. .................................. 544/257; 544/258; 544/260
[58] Field of Search ........................ 544/257, 258, 260

[56]  References Cited

U.S. PATENT DOCUMENTS

| 2,562,223 | 7/1951 | Weisblat et al. | 544/258 |
| 3,972,991 | 8/1976 | Caston et al. | 424/1.5 |
| 3,989,812 | 11/1976 | Barrett et al. | 424/1 |
| 4,091,087 | 5/1978 | Barrett et al. | 424/1 |
| 4,146,602 | 3/1979 | Gutcho et al. | 424/12 |

FOREIGN PATENT DOCUMENTS 2741677  3/1978  Fed. Rep. of Germany.

Primary Examiner—Paul M. Coughlan, Jr.
Attorney, Agent, or Firm—George W. Rauchfuss, Jr.

[57]  ABSTRACT

Folic acid derivatives, such as radiolabeled pteroyltyrosine, are conveniently synthesized from either pteroic acid or by the direct condensation of 6-formylpterin with p-aminobenzoyltyrosine methyl ester. The radioiodinated derivatives are particularly useful in competitive protein binding and radioimmuno-assays of folate compounds.

11 Claims, 1 Drawing Figure

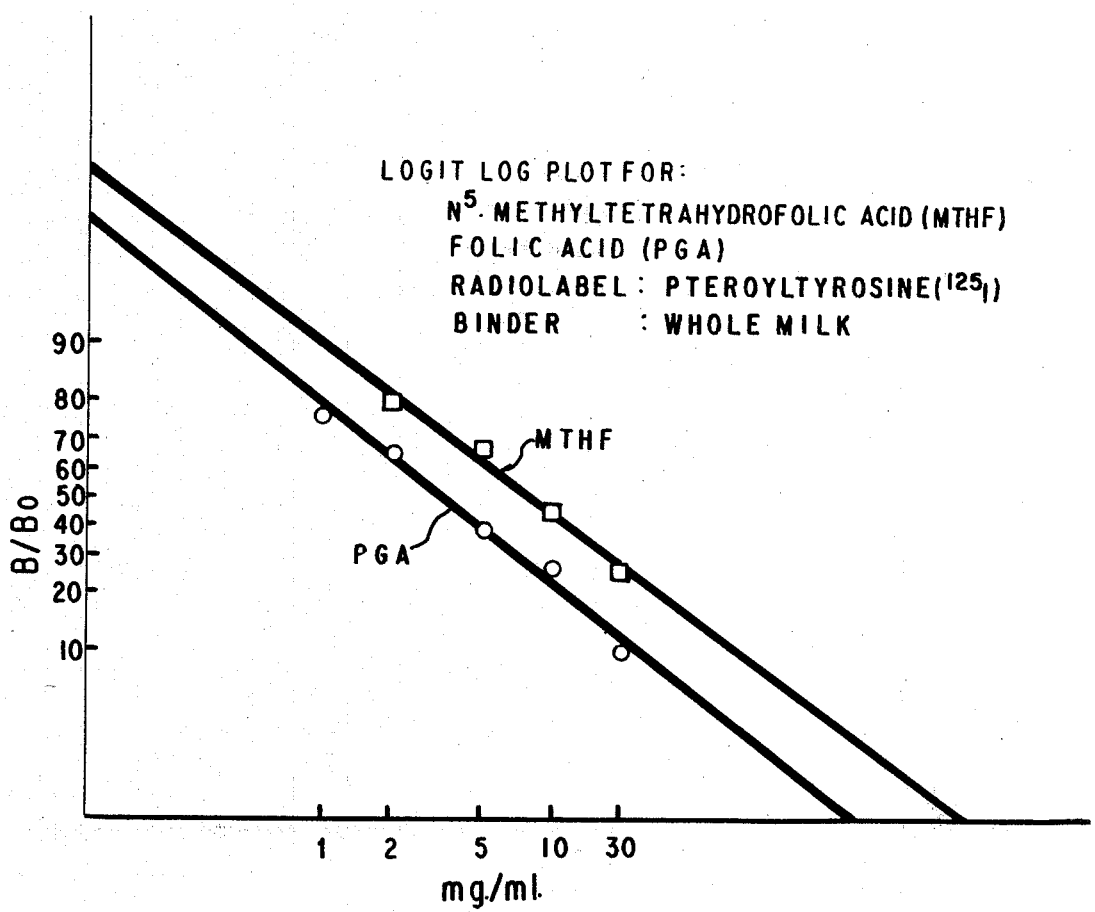

PROCESS FOR PREPARATION OF FOLIC ACID DERIVATIVES

This application is a division of our prior U.S. application Ser. No. 034,760, filed Apr. 30, 1979.

This invention relates in general to novel folic acid derivatives and to a process for their preparation. In one aspect, this invention is directed to folic acid derivatives which can be radioiodinated and are particularly useful in competitive protein binding and radioimmuno-assays of folate compounds. In another aspect, this invention relates to processes for the preparation of compositions which may be used as ligands in affinity chromatography or haptens in antigen syntheses.

In the 1940's, the structure of the vitamin, folic acid, was characterized and independently synthesized as reported by R. B. Angier et al., *Science*, 103, 667 (1946). This compound also known as pteroylglutamic acid (I) consists of a pterin, p-aminobenzoic, and glutamate moieties:

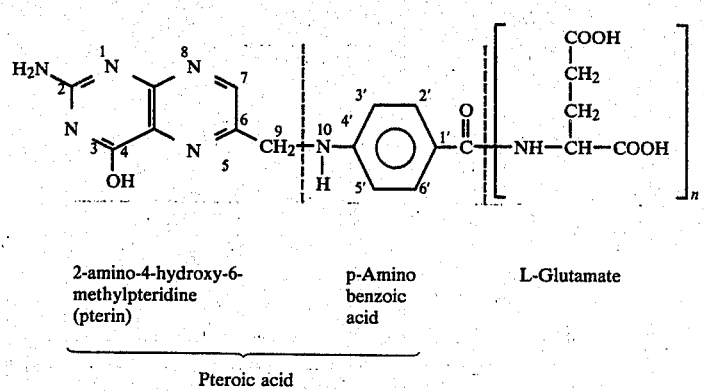

2-amino-4-hydroxy-6-methylpteridine (pterin)

p-Aminobenzoic acid

L-Glutamate

Pteroic acid

As indicated in the work of R. L. Blakley, The Biochemistry of Folic Acid and Related Pteridines, John Wiley and Sons, New York, 1969, folic acid is a requisite cofactor in the biological transfer of one carbon units at varying levels of oxidation. The measurement of folic acid and other folate cofactors or derivatives is of significant clinical value for the diagnosis of megaloblastic anemias, nutritional folate deficiencies such as those associated with alcoholism, and for monitoring dosage regimens in leukemia chemotherapy.

The most common, non-microbiological assay currently practiced utilizes a radioassay procedure based on competitive protein binding (CPB) between a radiolabeled folate derivative and a second "unknown" serum folate cofactor or drug. The technique is based on the ability of a specific binding protein and a specific ligand to form a reversible binder-ligand complex. As is well known, an assay is performed by adding a fixed quantity of radiolabeled ligand to a series of samples which contain the protein binder, and known amounts of a "standard" ligand. During incubation, radiolabeled ligand and unlabeled ligand compete for a limited number of sites on the binding protein. After incubation, bound ligand is separated from the free ligand and the ratio of free to bound can be plotted as a dose response curve. A serum sample can then be assayed by the same procedure and the concentration of the unknown determined by referring to the standard dose response curve.

An important, disclosed advance in radioimmunoassay has been the replacement in many cases of beta emitting tracers such as tritium and carbon-14 by the more readily monitored gamma emitters such as iodine (131 and 125) selenium (75) and cobalt (57 and 60). Unfortunately, in some instances the introduction of a large radiolabel such as iodine can alter or prevent binding of a radioligand to a binder. Thus, it is extremely important to design a precursor molecule which will undergo rapid iodination and will still be competitive under assay conditions.

This invention describes novel generic derivatives or analogs of folic acid I (and related compounds, such as folate metabolites and folate antagonist drugs), typified by pteroyltyrosine. These compounds were designed to approximate in size, as closely as possible, the cofactor, drug, metabolite, etc., but still permit facile iodination at a remote site. Previous approaches to folate [$^{125}$I] radiolabels involved the addition of a radioiodine accepting moiety to folic acid, whereas this disclosure describes the novel strategy of replacement of a significant portion of the folic acid molecule with a radioiodine acceptor. An additional advantage of the derivatives of this invention is that they can be conveniently synthesized and appear to be quite stable in the radioiodinated form.

Accordingly, one or more of the following objects can be achieved by the practice of this invention. It is an object of this invention to provide folic acid derivatives, such as radiolabeled pteroyltyrosine, pteroyltyramine, pteroylhistidine and the like. Another object of the invention is to provide derivatives or analogs of folates which can undergo facile, rapid labeling by radioiodine. A further object of this invention is to provide a process for the preparation of the folate compositions. A still further object is to provide a process for the quantitative detection of folates by the application of the radioiodinated compounds of this invention in competitive protein binding and radioimmuno-assays. Another object is to provide novel antigens, enzyme conjugates, immunosorbents and affinity ligands prepared from the coupling of the novel folate derivatives to proteins, enzymes, polypeptides, inorganic materials, polysaccharides or plastic articles. These and other objects will readily become apparent to those skilled in the art in the light of the teachings herein set forth.

The single drawing is a plot of dose response curves for folic acid and $N^5$ methyltetrahydrofolic acid obtained using pteroyltyrosine [$^{125}$I] prepared by the process of this invention. Further details on the procedure used are set forth in Example 7.

In its broad aspect this invention is directed to a class of novel folate derivatives, a process for their preparation in both unlabeled and labeled form, their application to radioassay and to in vivo diagnostic use, and the preparation of novel antigens, immunosorbents, and polymer bound forms of the genetic compounds.

The generic structure of the unlabeled form of the compounds prepared by the process of the instant invention can be illustrated as follows:

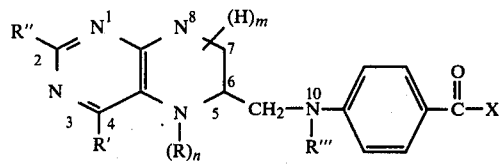

II wherein X represents a radiolabel acceptor as hereinafter defined; R represents hydrogen, lower alkyl, formyl or iminomethyl, R' and R" individually represent lower alkyl, hydroxyl, halo, amino or acetamido; R''' represents R or nitroso; m has a value of 1, 3 or 4 and n has a value of zero or 1. Thus, for example, when m equals 4 the ring containing nitrogen at the 5 and 8 positions will be saturated and the (R) group can be hydrogen or one of the substituents indicated above. Conversely, if the ring is unsaturated only one hydrogen will be present at the 7 position and n will be 0.

The structures of the compounds of this invention in the unlabeled forms, typified by pteroyltyrosine, can be viewed to be comprised of three linked components: a substituted pteridine moiety, a p-aminobenzoyl moiety, and a radiolabel acceptor. The latter two comprise the "dipeptide" portion of the generic structure.

It is important to note that the radiolabel acceptor component of this invention is not formed by the addition of an accepting moiety to folic acid, but by the replacement of the L-glutamate portion of the acid with such a component. Hence the X component of the above generic structure will not contain the L-glutamate moiety and the aromatic or heterocyclic group containing the radiolabel will be separated from the p-aminobenzoic acid moiety by a linear chain of no more than five atoms. The chain, of course, can be comprised of atoms other than carbon and can contain substituents and side chains which do not adversely affect its reactivity in competitive protein binding (CPB) and radioimmuno-assay applications.

The radiolabel acceptor groups which can be present in the compositions of this invention include those wherein X is a single amino acid or des-carboxy amino acid which contains a readily radioiodinated aromatic ring and a primary aliphatic amino group for attachment to the rest of the molecule via an amide bond. Illustrative X components of the generic structure II are groups such as the following which are derived from the indicated compounds:

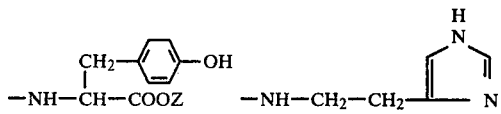

tyrosine (Z=H), histamine,

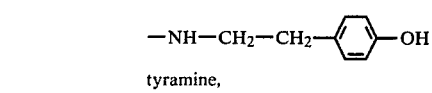

tyramine,

-continued

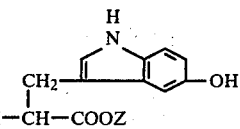

5-hydroxytryptophan (Z=H),

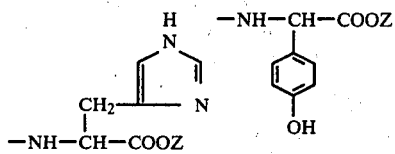

histidine (Z=H), 2(4'-hydroxyphenyl) glycine (Z=H), and the like, wherein Z is hydrogen or lower alkyl.

Preferred compositions of this invention are those wherein the X component or moiety contains up to 24 carbon atoms and more preferably up to 12 carbon atoms. As illustrated above, X can, of course, contain nitrogen and oxygen and other substituents which do not adversely affect the use of the compounds for CPB and radioimmunossay applications.

Variations in the pteridine portion of the molecule can be used to alter the performance of the subsequent radiolabel in a competitive protein binding or radioimmuno-assay, in order to gain specificity for primary metabolites of folic acid, folate antagonists used as drugs, and their metabolites. For example, radiolabeled species in which R=CH$_3$ or CHO, R'=OH and R"=NH$_2$, such as, N$^5$-methyltetrahydropteroyltyrosine-[$^{125}$I] and N$^5$-formyltetrahydropteroyltyrosine-[$^{125}$I], are appropriate labels in CPB and immuno-assays specific for N$^5$-methyl- and N$^5$-formyltetrahydrofolate, respectively. Similarly, species wherein R and N$^8$-H are absent R'=R"=NH$_2$, R'''=CH$_3$ and X is any suitable radioiodine acceptor (such as 4-amino-4-deoxy-N$^{10}$-methylpteroyl-[2-(4'-hydroxyphenyl)glycine]) are suitable markers for the CPB and immuno-assays of methotrexate.

In practice, the compounds of this invention can be prepared by a variety of methods. For example, pteroyltyrosine can be prepared by condensation of a protected pteroic acid with L-tyrosine methyl ester (L-TME) followed by basic hydrolysis to cleave both the ester and the protecting group. The sequence of reactions can be illustrated as follows:

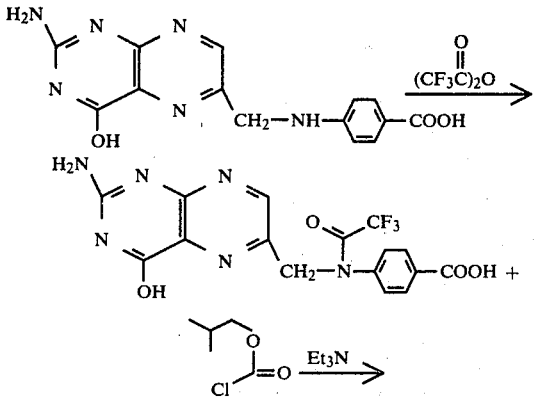

-continued

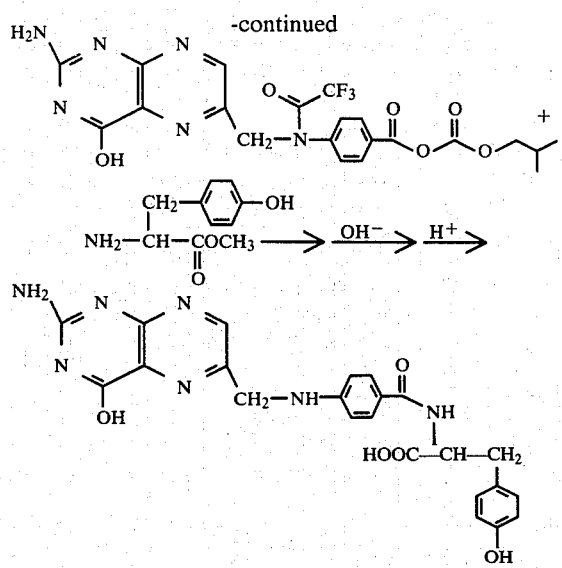

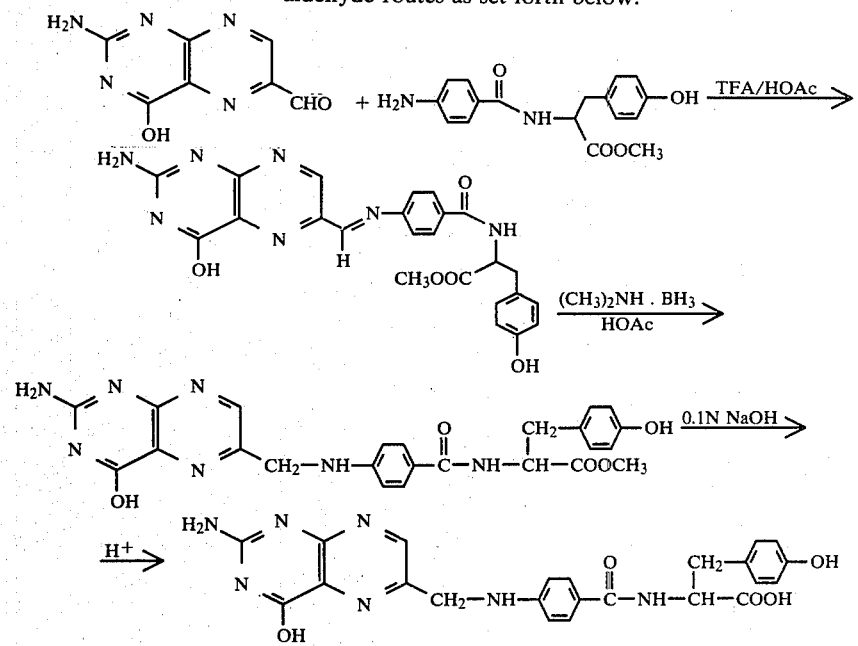

prepared from the reaction of pteroic acid with neat trifluoroacetic anhydride. The 2-amino group of pteroic acid does not require protection in this scheme because it is quite unreactive.

Condensation of $N^{10}$-trifluoroacetyl pteroic acid with L-TME was via the mixed anhydride procedure. The acid was treated with iso-butylchloroformate in an unreactive solvent (dimethylformamide) containing a tertiary amine base (triethylamine) to yield the mixed anhydride. This material was then treated with L-tyrosine methyl ester. Subsequent hydrolytic work up with dilute alkali metal hydroxide (0.1 N NaOH) and careful ion exchange column chromatography gave, after acidification, pteroyl-L-tyrosine.

A second approach to the synthesis of pteroyltyrosine was based on the condensation of a 6-formylpterin with a p-aminobenzoic acid ester or amide and reduction of the Schiff base formed to the $N^{10}$-secondary amine.

The pteroyltyrosine of the instant invention was prepared by a modification of the previously described aldehyde routes as set forth below.

Because the condensation conducted was between the carboxylic acid of pteroic acid and the amino group of L-TME, protection of the reactive $N^{10}$-nitrogen of pteroic acid was required so that it would not condense with itself in the coupling reaction. The protective group selected was the N-trifluoroacetyl group (N-TFA) which is readily removed via basic hydrolysis. The conditions employed for the hydrolysis of the ester (0.1 N NaOH, steam bath, 45 minutes under nitrogen) were more than adequate for the cleavage of the N-TFA group. $N^{10}$-trifluoroacetyl pteroic acid was The Schiff base between 6-formylpterin and p-aminobenzoyl-L-tyrosine methyl ester (H-PABA-L-TME) was formed in a 1:1 mixture of trifluoroacetic acid (TFA) and glacial acetic acid (HOAc) at room temperature. The solvents were then removed in vacuo and the residue was suspended in glacial acetic acid. Dimethylamine borane was added to reduce the Schiff base and afford pteroyltyrosine methyl ester. Basic hydrolysis of the ester moiety formed the product pteroyl-L-tyrosine.

A novel feature of the procedure was the use of trifluoroacetic acid in the solvent for the initial condensation. TFA is a powerful solvent for pteridine derivatives and its inclusion in high concentration allowed condensation of the generally quite insoluble 6-formylpterin with p-aminobenzoyltyrosine methyl ester to be conducted in homogeneous solution at high solute concentrations. Imine (Schiff base) formation is an acid catalyzed process, but in the presence of too strong an acid complete protonation of the amine will prevent condensation with the aldehyde. Trifluoroacetic acid is a very powerful acid, and ordinarily it would be a poor choice for imine formation. However, because of the low basicity of the amine involved (an aniline), protonation is not complete and reaction occurs quite rapidly in 50%

TFA/50% HOAc solution for the condensation shown in the above reaction. Neat trifluoroacetic acid and other powerful acid/solvent mixtures such as trichloroacetic acid/methylene chloride, trichloroacetic acid/acetic acid, methanesulfonic acid/acetic acid, and others could be used in this condensation provided the 6-formylpterin is soluble.

Prior to the reduction step the TFA or other strong acid must be removed from the Schiff base. Dimethylamine borane reduction of imines is generally conducted in glacial acetic acid. Strong acids such as TFA react rapidly with amine boranes and must be avoided in the reduction. Acetic acid on the other hand does not react with dimethylamine borane, or at least not competitively with the rather rapid imine reduction (half-time of minutes). Formic acid and other amine boranes can also be used to carry out the reduction step. In practice, it has been found that the amine boranes are preferred for their mildness, simplicity and rapidity.

A virtue in the choice of 6-formylpterin rather than $N^2$-acetyl-6-formylpterin in the synthesis of pteroyltyrosine and folate analogs of this type is that base treatment to remove an $N^2$-protective group is not required. Thus, the synthetic scheme above is compatible with preparation directly of a product which bears both a free $N^2$-nitrogen (amine group) and an ester in the radiolabel acceptor portion of the molecule. On the other hand, if an $N^2$-acyl group is desired in the final product one simply starts with the appropriate $N^2$-acylated 6-formylpterin derivative. Furthermore, one can prepare the free acid form of pteroylamino acid derivatives directly by starting with the free acid form of the p-aminobenzoyl peptide (such as p-aminobenzolyltyrosine or p-aminobenzoylhistidine, etc.) Pteroyltyrosine was prepared in this fashion from 6-formylpterin and p-aminobenzoyltyrosine, thereby obviating the final basic ester hydrolysis on the coupled product. In this particular reaction as shown in Example 1f(2), conditions were not optimized and the product obtained was less pure than that of coupling the ester followed by hydrolysis. Nevertheless, the pteroyltyrosine obtained from coupling p-aminobenzoyltyrosine could be radioiodinated to provide a radiolabel after purification (gel chromatography) which functioned identically in the folate competitive protein binding assay to that prepared from the hydrolyzed ester.

As previously indicated, folate [$^{125}$I] radiolabels prepared by prior art methods have consisted of an extension of folic acid by the covalent coupling of a radioiodine acceptor to one of the two glutamyl carboxyl groups. In addition to being conceptually different in design, the known folate [$^{125}$I] radiolabels share unattractive synthetic problems not encountered in the preparation of the compounds of this invention. Specifically, all of the known folate [$^{125}$I] radiolabels bear only one radioiodine acceptor attached to glutamate. Since the glutamyl residue contains two reactive carboxyl groups, synthesis of the desired "folic acid-extended" compound necessarily must involve either the resolution of a statistical mixture of one disubstituted plus two possible monosubstituted compounds, or extensive blocking and deblocking chemistry in several steps to protect one of the carboxyl groups and thereby direct the coupling toward the single desired locus.

In contrast to the known folate [$^{125}$I] radiolabels, pteroyltyrosine and its $^{125}$I derivative represent a novel strategy for the design of folate radiolabels wherein a portion of the folic acid molecule, namely the glutamate moiety, is replaced by a radioiodinatable group. This strategy is employed in order to approximate the species to be assayed in molecular size as closely as possible. This approach is unique because in modifying the molecule in this fashion one runs the risk of eliminating structural features important or necessary for protein binding while one is striving to maintain approximate molecular dimensions in order to insure good binding. This strategy has been demonstrated with pteroyltyrosine [$^{125}$I] as the radiolabel in a folate CPB assay sensitive in the clinically significant concentration range. In addition, the compounds of this invention are readily synthesized by straightforward routes which avoid some of the complexities inherent in the syntheses of known folate [$^{125}$I] radiolabels.

That the generic compounds of this invention can be mildly and rapidly radioiodinated was demonstrated by the radioiodination of pteroyltyrosine to give the compound:

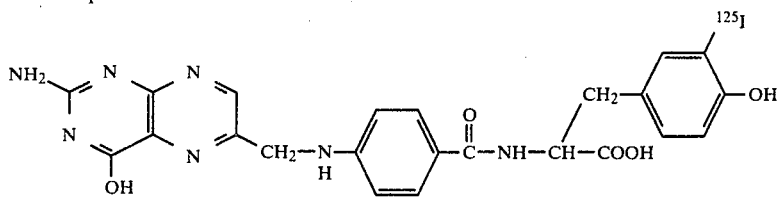

Typically, iodine uptake of about 90 percent was observed in the labeling of 2.5–5.0 μg of pteroyltyrosine with 1 mCi of $^{125}$I. The reaction mixtures were fractionated on short gel filtration columns and the several fractions at the very maximum of the major radioiodinated peak of the gel chromatogram were pooled for use in the radioassay.

The generic compounds of this invention in their radioiodinated form are designed to serve as radiomarkers in CPB and immuno-assays. To this end the appropriate choice of substituents allows the synthesis of radiolabels for the detection and quantification of species such as folic acid, methotrexate (a cancer chemotherapeutic folate antagonist), and major metabolites and/or important circulating forms of folic acid and methotrexate and other potential folate antagonists. It has been verified that pteroyltyrosine [$^{125}$I] is an effective radiolabel in a sensitive CPB radioassay for folic acid in the concentration range of 0–20 ng/ml. Furthermore, it has been demonstrated that variation of assay parameters such as buffer, pH, and nature of protein binder can be exploited to modulate the response of the assay to the two major circulating forms of folate: folic acid and N-5-methyltetrahydrofolic acid ($N^5$-methyl THF). Thus at high pH the dose response curves for folic acid and $N^5$-methyl THF generated using pteroyltyrosine [$^{125}$I] as label are more nearly coincident than at lower pH.

Radioiodination of biological compounds frequently leads to marked chemical instability and subsequent degradation of the radiolabel. This problem is often accentuated in the radiolabel when the materials to be radioiodinated are known to be sensitive to oxygen, light or extremes in pH, as is the case with folic acid and some derivatives. An important feature of this invention is the remarkable stability of the radioiodinated product pteroyltyrosine [$^{125}$I] which shows no deterioration in assay performance over a ten-week period when stored in a 50% aqueous propylene glycol solution.

Radioiodination of compounds of this invention can be effected by one or more methods known in the art and shown in the examples. Alternative procedures for the radioiodination of the molecules of this invention, such as the lactoperoxidase, electrolytic, and iodine monochloride methods can also be employed and may in certain instances (e.g., sensitivity of precursor to organic oxidants) be preferred. Variations in the radiolabel which can be introduced to the X moiety include: $^{125}$I, $^{131}$I, and $^{123}$I.

In another embodiment of this invention it is known that the inherent reactivity of the group X in the generic formula toward electrophilic aromatic substitution (e.g., radioiodination) permits simple covalent immobilization to insoluble support materials. For example, diazotized poly (p-aminostyrene) can react rapidly with the compounds of this invention to yield azo-linked products (see Example 9). In certain cases the group X of compound II contains additional functionality, such as carboxylic acids when X is an amino acid, with which the compounds of this invention may be coupled to macromolecules (Example 10). Insolubilized (immobilized) forms of the novel compounds described herein have utility as affinity sorbents for the separation and purification of enzymes, antibodies, binding proteins and other molecules which form complexes with folic acid, methotrexate, and related metabolites, analogs, and derivatives.

The following examples are illustrative:

EXAMPLE 1

PREPARATION OF PTEROYLTYROSINE FROM 6-FORMYLPTERIN (a) N-Carbobenzoxy-p-aminobenzoic acid (Z-PARA-OH)

A 500 ml, round-bottom, three-neck flask was charged with 300 ml of water, 33.55 g (0.40 mole) of sodium bicarbonate, and 19.33 g (0.14 mole) of p-aminobenzoic acid (PABA). The resultant solution was stirred mechanically as 25.0 ml (30.0 g, 0.18 mole) of carbobenzoxy chloride was added dropwise over a period of one hour. Once addition was complete, the thick, white suspension which had formed was allowed to stir overnight. This suspension was suction filtered, and further work-up of both the filtrate (A), and the filtered solid (B) afforded the desired product. The filtrate (A) was acidified with concentrated hydrochloric acid to pH 1, and the white precipitate which formed was isolated by filtration and washed with water until the filtrate was neutral. This precipitate was dissolved in 1 N NaOH and extracted with 100 ml of ether. The ether layer was back extracted twice with 60 ml of 1 N NaOH and these extracts were pooled with the first aqueous layer. Acidification of the pooled basic layer to pH 1 yielded a copious white precipitate which was collected on a filter and washed with water until a filtrate was neutral. The moist solid was freed of water by dissolving it in ethyl acetate (EtOAc, 200 ml), draining off the several milliliters of water which rapidly settled out, drying over magnesium sulfate, and taking the colorless solution to dryness in vacuo. Yield 6.05 g of Z-PABA-OH as a white powder.

Additional product was isolated from the original filter cake (B) in similar fashion by first dissolving it in 1 N NaOH, washing with ether, and acidifying the aqueous layer to pH 1 with concentrated HCl. The resultant white precipitate was collected on a filter washed with water, and then freed of water and taken to dryness as above. Yield: 20.16 g of white solid. This was further purified by recrystallization from acetone-cyclohexane. A total of 16.85 g of crystalline Z-PABA-OH was obtained in three crops, m.p. 217.0–218.0 (dec).

Over-all yield 22.90 g (60%).

Anal. Calcd. for $C_{15}H_{13}NO_4$: C, 66.41; H, 4.83; N, 5.16. Found: C, 66.26; H, 4.64; N, 5.16.

nmr (DMSO,$d_6$;$\delta$): 5.25 (s, 2H, benzyl $CH_2$); 7.45 (s, 5H, Cbz aromatic); 7.87 (center of gravity for $A_2B_2$ "quartet", 4H, PABA aromatic); 10.17 (s, 1H, COOH).

ir (KBr,$\mu$): 5.90, 5.99 (doublet, urethane and acid).

UV (methanol): $\mu_{max}$ 258 nm (24,500).

(b) N-Carbobenzoxy-p-aminobenzoyl-L-tyrosine-methyl ester (Z-PABA-TME)

Z-PABA-OH (9.60 g, 0.035 mole) was dissolved in 175 ml of tetrahydrofuran (THF) in a 500 ml, round-bottom flask containing a magnetic stirring bar. The solution was cooled in an ice-salt-water bath to $-10°$ C. N-methyl morpholine (4.12 ml, 0.037 mole) was added all at once, followed shortly thereafter by the addition of 4.8 ml (5.05 g, 0.037 mole) of iso-butyl chloroformate. A milky white suspension was formed which was stirred magnetically for five minutes. To the suspension at $-10°$ C. was added dropwise with stirring, a solution of L-tyrosine methyl ester (7.60 g, 0.039 mole) in 25 ml of dimethylsulfoxide plus 75 ml of THF over the course of fifteen minutes. Once addition was complete, the reaction mixture was stirred at $-10°$ C. for 2–3 hours. It was then allowed to warm to room temperature and was stirred overnight. The mixture was filtered, the precipitate was washed with THF, and the combined filtrate was concentrated with gentle warming (30°–35° C.) on the rotary evaporator. The residue, a viscous yellow DMSO solution, was treated with water (100 ml) and ethyl acetate (200 ml). After being shaken the aqueous layer was separated and the organic layer was extracted twice more with 100 ml portions of water. The EtOAc layer was dried over $MgSO_4$, filtered, and taken to dryness on the rotary evaporator. Recrystallization of the residue from ethyl acetatecyclohexane afforded 5.88 g (37%) of Z-PABA-L-TME, m.p. 171.5°–172.0° C., $[a]_D^{25}-67.2°$ (c=1.0, methanol).

Anal. Calcd. for $C_{25}H_{24}N_2O_6$: C, 66.95; H, 5.39; N, 6.24. Found: C, 66.72; H, 5.25; N, 6.26.

nmr (acetone, $d_6$; $\delta$): 3.08 (asym. d, J=8 Hz, 2H, Tyr $CH_2$); 3.67 (s, 3H, $CH_3$); 4.85 (m, 1H, Tyr CH); 5.18 (s, 2H, Cbz $CH_2$); 6.95 (center of gravity for $A_2B_2$ "quartet", 4H, Tyr aromatic); 7.38 (s, 3H, Cbz aromatic); 7.73 (center of gravity for $A_2B_2$ "quartet", 4H, PABA aromatic).

ir (KBr pellet, $\mu$): 5.8–5.9 (broad; amide, ester and urethane).

UV (methanol); $\mu_{max}$ 265 nm (30,700).

(c) p-Aminobenzoyl-L-tyrosine methyl ester (H-PABA-L-TME)

Into a 200-ml, round-bottom flask containing a magnetic stirrer and equipped with a gas inlet tube was placed 2.38 g (5.31 mmole of Z-PABA-L-TME) and 60 ml of methanol. To the solution was added about 265 mg of 5% palladium on carbon which had been twice washed with 3 ml portions of methanol. Hydrogen gas was bubbled through the stirred suspension for an hour, then an additional 265 mg of washed catalyst was added and the bubbling of hydrogen was continued for an additional two hours. At the end of this time, no trace of $CO_2$ could be detected in the effluent gas with saturated barium hydroxide solution. The catalyst was removed by filtration through a Standard Super Cell pad (J.M.) and was washed with a copious amount of boiling methanol. The filtrate was taken to dryness on the rotary evaporator, affording a tan crystalline residue (1.58 g, 95% crude yield). Recrystallization from 200 ml of chloroform containing a minimum of ethyl acetate (5–10 ml) provided 1.44 g (86%) of H-PABA-L-TME as light tan needles, m.p. 169.5°–170.5° C., $[a]_D^{25} -76.4°$ (c=1.0, methanol).

Anal. Calcd. for $C_{17}H_{18}N_2O_4$: C, 64.49; H, 5.77; N, 8.91. Found: C, 64.80; H, 5.63; N, 9.08.

nmr (DMSO, $d_6$,): 2.98 (asym. d, J=8 Hz, 2H, Tyr $CH_2$); 3.56 (s, 3H, $CH_3$); 4.55 (m, 1H, Tyr CH); 5.63 (s, 2H, Cbz $CH_2$); 6.3–7.8 (eight resonances, 8H, pair of aromatic $A_2B_2$ "quartets"); 8.62 (d, J=8 Hz, 1H, amide NH).

ir (KBr, $\mu$): 5.79 (ester); 6.19 (amide
UV (methanol); $\lambda_{max}$ 281 nm (21,100).

(d) p-Aminobenzoyl-L-tyrosine (H-PABA-L-Tyr-OH)

A sample of H-PABA-L-TME (1.06 g, 3.37 mmole) was dissolved in 150 ml of 0.1 N NaOH with swirling. After 1.5 hours the solution was extracted with 50 ml of EtOAc, and the organic layer was discarded. The aqueous layer was acidified to pH 5–6 with concentrated HCl and was extracted with EtOAc (4×50 ml). The pooled EtOAc layer was washed with water (3×50 ml) and was taken to dryness on the rotary evaporator, affording 0.41 g of a tan foam. The original aqueous layer was further acidified to pH 3.4–3.8 and again was extracted with EtOAc (2×20 ml and 1×30 ml). These EtOAc extracts were pooled and washed with water (4×30 ml). Concentration of the organic layer on the rotary evaporator gave 0.32 g of a colorless foam. The two residues were pooled and recrystallized from EtOAc to yield 280.8 mg of tan micro-fine prisms:

m.p. 178.5°–180° C., $[a]_D^{25} -59.4°$ (c=1.0, methanol). The nmr spectrum of this material revealed the presence of EtOAc despite having dried the sample at room temperature in vacuo (0.1 mm Hg) for several hours. Apparently the dipeptide crystallized as the ethyl acetate solvate; roughly 0.5 mole of EtOAc per mole H-PABA-L-Tyr-OH was present in the crystalline sample after drying.

nmr (DMSO, $d_6$; $\delta$); 1.17 (t, J=7 Hz, ethyl $CH_3$ of EtOAc); 1.98 (s, $CH_3CO$ of EtOAc); 3.0 (asym. d, J=7 Hz, 2H, Tyr $CH_2$); 4.05 (q, J=7 Hz, $CH_2$ of EtOAc); 4.55 (m, 1H, Tyr CH); 6.4–7.8 (eight resonances, 8 H, pair of aromatic $A_2B_2$ "quartets"); 8.07 (d, J=8 Hz, 1H, amide NH, exchangeable).

UV (methanol): $\lambda_{max}$ 278 nm (25,900).

(e) Pteroyl-L-tyrosine methyl ester (Pt-L-TME)

A 50 ml round-bottom flask containing a magnetic stirring bar was charged with 120.5 mg (0.63 mmole) of 6-formyl pterin, prepared by the method of Viscontini, et al., (1) (2) 490.2 mg (156 mmole, 2.47 equiv.) of (1) M. Viscontini, R. Provenzale, S. Ohlgart and J. Mallevialle, *Helv. Chim. Acta.*, 53, 1202 (1970).

(2) M. Viscontini and J. Bieri, *Helv. Chim. Acta.*, 54, 2291 (1971).

H-PABA-L-TME and 4 ml of glacial acetic acid (HOAc). With stirring the H-PABA-L-TME dissolved, but the yellow aldehyde remained in suspension. The flask was flushed with argon as 3–4 ml of trifluoroacetic acid (TFA) was slowly added to effect complete dissolution of the suspended solids. Stirring was continued for an additional 30 minutes from this point. Most of the solvent then was removed from the dark brown solution by gentle warming (40° C.) on the rotary evaporator (water aspirator). The moist brown residue was taken to dryness under high vacuum (0.05 mm Hg) at room temperature overnight with the flask wrapped in aluminum foil to exclude light. A brown foam or glass resulted. The vacuum was broken and argon was bled into the flask. To the brown foam was added 4 ml of HOAc, and with vigorous swirling and stirring (under argon) the residue was dislodged from the walls of the flask to form a light yellow-brown suspension. Dimethylamine borane, 37.2 mg (0.631 mmole, 1 equiv.) was added to the stirred suspension; the color rapidly changed to orange-brown and nearly all of the solid dissolved. After an hour HOAc (8–10 ml) was used to rinse down the neck and walls of the flask. The reaction mixture was concentrated with gentle heating (40°) on the rotary evaporator to a viscous residue. Two 25 ml portions of toluene were successively added to the residue, mixed, then stripped in vacuo with gentle warming to remove HOAc as its toluene azetrope. The final toluene-damp residue was dried to a brown foam under high vacuum at room temperature overnight. To the flask was added 30 ml of EtOAc. The foam was scraped from the walls of the flask with a metal spatula to form a suspension, which was left standing in the refrigerator overnight. The insoluble yellow-orange solid was separated from the yellow supernatant by centrifugation. The pelleted solid was resuspended in EtOAc and recentrifuged three times until the final EtOAc wash was colorless. Finally, the pelleted solid was resuspended in a small volume of EtOAc, collected on a coarse fitted glass filter under argon in a pressure filtration apparatus, washed with several small portions of EtOAc and dried by flowing argon through the collected filter cake under positive pressure for an hour.

Yield: 174 mg (56%) buff-colored powder, pteroyl-L-tyrosine methyl ester.

m.p. 230–350 (slowly decomposed).

nmr (DMSO, $d_6$; $\delta$): 3.59 (s; 3H, ester $CH_3$); 4.48 (broad s, 3H, C-9 $CH_2$ and Tyr CH); 6.6–7.6 (six line multiplet, 8H, overlapping pair of aromatic $A_2B_2$ "quartets"); 8.30 (d, J=8 Hz, amide NH, exchangeable); 8.65 (s, 1H, C-7 H).

Mass Spectrum (field desorption); m/e 489 (100%), 314, 207, 192.

(f) Pteroyl-L-Tyrosine (Pt-L-Tyr-OH)

(1) Hydrolysis of Pt-L-TME

To a 50 ml round-bottom flask containing 122.0 mg (0.25 mmole) of pteroyl-L-tyrosine methyl ester under argon was added 10 ml of 0.1 N NaOH which had been rigorously degassed by sparging with argon. The flask was stoppered and shaken for ten minutes to dissolve the solid; a dark yellow-brown slightly turbid solution resulted. After an additional 35 minutes at room temperature the turbid reaction mixture was filtered through a mixed cellulose ester Millipore filter (1.2μ nominal pore size). The clear, brown filtrate was acidified to pH 2 with 1.0 N HCl and a voluminous, gelatinous brown precipitate was formed. The suspension was centrifuged at 14,000 rpm in the cold (4°-5° C.) for 15 minutes, and the supernatant liquid was decanted. The pelleted solid was washed successively with 0.1 N HCl (2×20 ml), distilled water (2×20 ml), absolute ethanol (2×20 ml), and ethyl ether (2×20 ml) by resuspension and recentrifugation. The washed solid was dried under high vacuum at room temperature to yield 6.1 mg (52%) of a dark-brown solid (Pt-L-Tyr-OH).

UV (0.1 N NaOH): $\lambda_{max}$ 249 (25,500), 283 (21,700), 362 nm (7,800); acidified to pH 1.8 with conc. HCl: $\lambda_{max}$ 224 (29,500), 256 (25,200), 280 nm (18,200).

nmr (DMSO, $d_6$; δ): 4.46 (m, 3H, C-9 $CH_2$ and Tyr CH); 6.6-7.6 (six resonances, 8H, overlapping pair of aromatic $A_2B_2$ "quartets"); 8.13 (d, J=8 Hz, 1H, amide NH, exchangeable); 8.64 (s, 1H, C-7 H).

Mass Spectrum (Field Desorption): m/e 475 (M+), 457, 429, 415, 413, 313, 312, 300, 293, 282, 268.

(2) Condensation of 6-Formylpterin with H-PABA-L-Tyr-OH

A 25 ml round-bottom flask containing a magnetic stirring bar was wrapped in foil to exclude light and purged with argon. A sample of 6-formylpterin (109.0 mg, 0.57 mmole) was added to the flask and dissolved by the addition of 1.0 ml of TFA. After 15 minutes of stirring all of the aldehyde had dissolved, forming a bright, yellow solution. H-PABA-L-Tyr-OH (216.0 mg, 0.72 mmole), 1.26 equiv.) was added all at once, and to hasten dissolution an additional 1.0 ml of TFA was added. Fifteen minutes of continuous swirling and stirring were required to effect complete dissolution. A dark, brown solution resulted which was stirred for an additional 40 minutes. The solvent was stripped in vacuo, affording a thick brown oil which still contained TFA. HOAc (7 ml) was added to the oil and a suspension of a fine yellow solid in a dark, brown supernatant liquid resulted. This was taken to dryness at 45°-50° C. on the rotary evaporator. The yellow-brown residue was resuspended in HOAc (2 ml), and 26.2 mg (0.28 mmole) of pyridine borane was added all at once. After 30 minutes the acetic acid was stripped on the rotary evaporator at 49° C., yielding a brownish-yellow solid residue. The residue was suspended in 10 ml of degassed EtOAc, filtered under argon, and dried by positive flow of argon through the filter cake for 30 minutes.

Yield: 224.3 mg of crude Pt-L-Tyr-OH. The nmr spectrum of this material clearly contained resonances coincident with those of the more pure sample prepared by hydrolysis of Pt-L-TME above. However, unassigned resonances in the spectrum suggested the material was only 30-50% pure. A sample of this material (200 mg) was further purified by dissolution in 10 ml of 0.1 N NaOH and precipitation by acidification to pH 2.5 with 1.0 N HCl. The collected solid (centrifugation) was washed twice with absolute ethanol and twice with ether and dried in vacuo to yield 100 mg of brown solid. Direct radioiodination of this latter material afforded an isolable fraction which behaved in the folate competitive protein binding assay identically to Pt-L-Tyr-OH [$^{125}$I].

EXAMPLE 2

PREPARATION OF PTEROYL-L-HISTIDINE (PT-L-HIS-OH)

By the method of Example 1b, one prepares N-carbobenzoxy-p-aminobenzoyl-L-histidine methyl ester (Z-PABA-L-His-OMe) from one part of histidine methyl ester and one part of Z-PABA-OH. Catalytic hydrogenolysis of Z-PABA-L-His-OMe by the method of Example 1c produces a high yield of p-aminobenzoyl-L-histidine methyl ester (H-PABA-L-His-OMe), which is then employed in the reductive amination of 6-formylpterin by the method of Example 1e to yield pteroyl-L-histidine methyl ester (Pt-L-His-OMe). Subsequent basis hydrolysis of Pt-L-His-OMe by the method of Example 1f(1) affords the final product Pt-L-His-OH.

EXAMPLE 3

PREPARATION OF PTEROYLTYRAMINE

Pt-L-Tyra is prepared by the method of Example 1 except that tyramine is employed instead of tyrosine methyl ester, and final basic hydrolysis (Example 1f(1)) is obviated since tyramine does not contain a carboxylic acid ester.

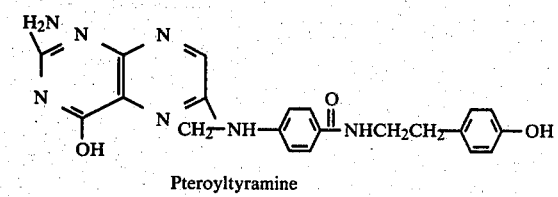

Pteroyltyramine

EXAMPLE 4

PREPARATION OF PTEROYLTYROSINE FROM PTEROIC ACID (a) Synthesis of $N^{10}$-trifluoroacetylpteroic Acid Pteroic acid (130 mg) was refluxed with trifluoroacetic anhydride for 6 hours at which time dissolution was complete. The solution was evaporated, under reduced pressure, and triturated with water (1 ml) to give a yellow solid. The amorphous material was washed 3 times with 5 ml portions of water, centrifuged each time, and dried in vacuo overnight.

(b) Pteroyltyrosine $N^{10}$-Trifluoroacetylpteroic acid (87.5 mg) and triethylamine (0.034 ml) was dissolved in N,N-dimethylformamide (2 ml). Iso-butyl chloroformate (0.045 ml) was added to the mixture and the solution was stirred under nitrogen at 30°, for 45 min., after which an additional quantity of triethylamine (0.090 ml) was added followed by L-tyrosine methyl ester (124 mg), and stirred at 30° for 24 hours. The reaction mixture was then poured into 0.1 N NaOH (36 ml) and heated on a steambath, under a nitrogen atmosphere for 45 mins. After cooling in an ice-bath, the solution was adjusted to pH 2 with concentrated hydrochloric acid, which gave a gelatinous precipitate. The precipitate was centrifuged and washed 3 times with small portions of water. The gel was dissolved in 1.0 M ammonium bicarbonate (50 ml) diluted to 500 ml with water and chromatographed on a column of DEAE-cellulose (1.5×25 cm). The column was eluted with ammonium bicarbonate (0.5 M) and the product was detected in the fractions appearing after 800 ml of eluant was collected.

The ammonium bicarbonate solution of the derivative was evaporated under reduced pressure and repeatedly evaporated with additional quantities of water until the salts had evaporated. Dissolution of the residue in water and acidification with hydrochloric acid to pH 2.5 gave a precipitate which was centrifuged, washed with water, ethanol, ether and then dried in vacuo.

Mass Spectrum (Field Desorption): m/e 475 (M+), 458, 457, 429, 413, 309, 300, 293.

UV (0.5 N NaOH): $\lambda_{max}$ 252, 281, 364 nm; (0.5 N HCl) $\lambda_{max}$ 218, 246 (sh), 282 (sh), 302 nm.

EXAMPLE 5

IODINATION OF PTEROYLTYROSINE

To a mixture of 1.0 millicurie of sodium iodide-$^{125}$I in 2.5 μl of solution, 25 μl of 0.5 M potassium phosphate buffer, pH 7.5 and 2.5 μg of pteroyltyrosine in 25 μl buffer in a disposable 1.5 ml microsample tube was added at once 50 μg of chloramine T (N-chloro-p-toluenesulfinamide, sodium salt trihydrate), in 20 μl of 0.05 M potassium phosphate buffer, pH 7.5. After exactly 20 seconds, 100 μg of sodium metabisulfite dissolved in 20 μl of 0.05 M potassium phosphate buffer was added, at once, to terminate the reaction.

The reaction mixture was applied to a 1×20 cm Sephadex G25, fine, (Pharmacia Fine Chemicals, Uppsala, Sweden) column hydrated with distilled water and equilibrated with 0.1 M potassium phosphate, pH 7.5. The column was eluted with 0.1 M potassium phosphate buffer and 3 ml fractions collected. The product "peak" fractions 32-34 were collected, diluted 1:1 with propylene glycol and stored below 0° C.

EXAMPLE 6

IODINATION OF PTEROYL-L-(5-HYDROXYTRYTOPHAN)

Pteroyl-L-(5-hydroxytryptophan), which is prepared by the method of Example 1 using L-5-hydroxytryptophan methyl ester instead of L-tyrosine methyl ester, is iodinated and purified by the method of Example 5 to yield pteroyl-L-(5-hydroxytryptophan) [$^{125}$I].

EXAMPLE 7

COMPETITIVE PROTEIN BINDING ASSAYS FOR FOLIC ACND N$^5$-METHYLTETRAHYDROFOLIC ACIDS

An application of the novel generic radioiodinated folate derivatives, typified by pteroyltyrosine [$^{125}$I], is the use of these radiolabels in competitive protein binding radioassays for folate constituents in human blood serum. The use of the Centria® analytical system, Union Carbide Corporation, in this example, is meant to be illustrative and other methods, both automated and manual, obvious to those skilled in the clinical diagnostic art are also within the scope of this invention.

Briefly, the Centria® system is a tri-modular instrument in which reagents are pipetted on to a multiwell transfer disk and mixed centrifugally with standards or patients' samples. After a suitable incubation period, the components are separated by a centrifugal elution of the bound and free fractions and the bound fractions counted three at a time. The data reduction, performed by a micro-processor is given selectively as either raw counts percent bound or in conventional units from a standard curve derived using one of several transforms.

Folic acid and N$^5$-methyltetrahydrofolic acid standards in the range 0-20 nanograms/milliliter were prepared in 0.05 M sodium borate, pH 9.3 containing 0.1% human serum albumin. The whole milk binder was prepared according to the method of Rothenberg et al., (3) and dissolved in sodium borate, pH 9.3 containing 0.1% human serum albumin.

In detail, aliquots of folate standards or unknowns (15 microliters) were permitted to compete after centrifugal transfer and mixing with pteroyltyrosine [$^{125}$I] (50 microliters, 20,000 cpm) plus 85 microliters of water with the limited number of binding sites contained in a 200 microliter solution of whole milk folate binder. The binding reactions may be shown as follows:

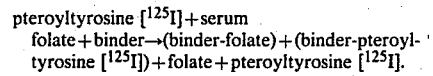

After a 10 minute incubation, the reaction mixture was centrifugally transferred onto DEAE Sephadex A-25 columns (0.75×4 in.) where separation of complexed folate from free folate was effected with 1.4 ml of elution buffer (3) S. Rothenberg, M. DaCosta, and Z. Rosenberg, New Eng. J. Med., 286, 1335 (1972). (0.05 M sodium borate, pH 9.3) per sample tube, with the following results:

In the eluant:

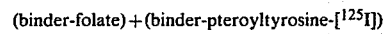

On the column:

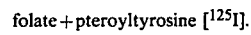

A gamma counter which counts three of the 36 positions at a time for one minute, so constructed that only the eluate bottom portion of the test tubes fits into the counter, was then used to count all samples. Sequential counting of the tubes thus required about 12 minutes. A small computer with printout capability then printed out the data after completion of the cycle. A logit-log plot of dose response curves for folic acid and N$^5$-methyltetrahydrofolic acid is presented in the Figure.

EXAMPLE 8

ENZYMATIC HYDROLYSIS OF PTEROYLTYROSINE

Two mililiters of a solution of pteroyltrosine (0.75 mmoles/ml) in 0.025 M Tris-HCl containing 2 mM zinc chloride, pH 7.3 were diluted to 10 ml with distilled water. A portion of this solution (2 ml) was placed in a 1 cm cuvette and in another was placed 2 ml of distilled water. To each of the cuvettes was added 50 μl of a solution of 100 μl carboxypeptidase A suspension (Aldrich chemical, lot (060637) diluted with 0.9 ml of 10% lithium chloride.

The time course of the reaction was followed spectrophotometrically (uv) over a period of two hours at ambient temperature. An increase and shift in max from 280 to 277 nm and a marked decrease in absorption at 220 nm was observed. Two isobestic points at 242 and 282 nm were visible. The final spectrum was very similar to that of pteroic acid.

EXAMPLE 9

PREPARATION OF AN AFFINITY CHROMATOGRAPHIC MEDIUM FOR PURIFICATION OF FOLATE BINDING PROTEINS CROSS-REACTIVE WITH PTEROYL-L-TYROSINE

Poly(p-aminostyrene) (2 g) is swollen in a mixture of DMSO/3 N HCl (1:1, 15 ml) and cooled to 0° C. in an ice bath. The mixture is gently agitated (stirring, swirling) as solid sodium nitrite (54 mg, 0.64 mmole) is added in several small portions over the course of 5 minutes. After the last portion of sodium nitrite is added the reaction mixture is filtered in the cold (0°–5° C.) and quickly washed with three 25 ml portions of cold DMSO/H$_2$O (1:1). The moist resin is then quickly added to a solution of pteroyl-L-tyrosine (100 mg, 0.21 mmole) in 10 ml of DMSO/0.5 N NaOH (1:1). The pH is readjusted to 10–11 with cold 4 N NaOH and maintained at this pH as the reaction is allowed to proceed with gentle agitation in the dark at 0°–6° C. The mixture is then allowed to warm to room temperature for an hour, acidified to pH 5 with 1 N NaOH and stirred at ambient temperature for an additional half hours.

The mixture is filtered and the resin is washed with copious quantities of DMSO/water (1:1), then distilled water until no further elution of pteroyl-L-tyrosine can be detected by radioassay. The water-wet resin is then washed thoroughly with methanol and methylene chloride, successively, dried of methylene chloride in vacuo, and stored dry, in the cold, protected from light.

EXAMPLE 10

CONJUGATION OF PTEROYL-L-TYROSINE TO BOVINE SERUM ALBUMIN. A NOVEL FOLATE ANTIGEN

A solution of pteroyl-L-tyrosine (100 mg, 0.21 mmole) and tri-n-butylamine (45 mg, 0.24 mmole) in DMSO (15 ml) is cooled to 5°–6° C., and iso-butyl chloroformate (33 mg, 0.24 mmole) is added with stirring. The reaction mixture is stirred for 15 minutes at 5°–6° C. and then added all at once with stirring to a cold (5° C.) solution consisting of bovine serum albumin (1.0 g, 1.4×10$^{-5}$ mmole) dissolved in 10 ml of distilled water and adjusted to pH 9.0 with 5% (W/V) potassium carbonate. The reaction mixture is maintained at pH 9.0 with 5% potassium carbonate solution while being stirred at 5° C. for 4 hours, followed by stirring at ambient temperature for 1 hour. The mixture/solution is filtered if necessary through a Millipore filter (mixed cellulose ester, 0.5μ) and then dialyzed against 2 l volumes of distilled water changed once daily for five days. The conjugate solution is lyophilized to a fluffy powder.

Although the invention has been illustrated by the preceding examples, it is not to be construed as being limited to the materials employed herein, but rather, the invention encompasses the generic area as hereinbefore disclosed. Various modifications can be made without departing from the spirit and scope thereof.

What is claimed is:

1. A process for the preparation of a composition having the formula:

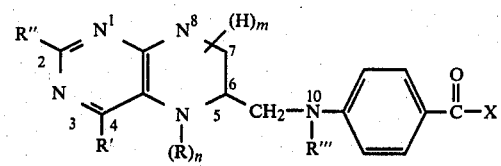

wherein R represents hydrogen, lower alkyl, formyl or iminomethyl; R' and R" individually represent lower alkyl, hydroxyl, halo, amino or acetamido; R'" represents H or lower alkyl; m has a value of 1, 3 or 4; n has a value of zero or 1; and X is an amino acid or des-carboxy amino acid moiety; selected from the group consisting of:

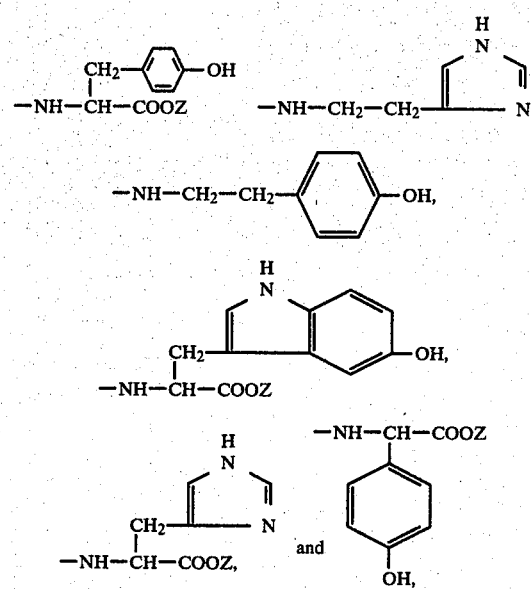

wherein Z is hydrogen or lower alkyl, said process comprising the steps of:
  (a) contacting a pteroic acid of the above formula wherein X is —OH, with a blocking agent to protect the nitrogen at the 10 position when R'" is H.
  (b) contacting the pteroic acid of step (a) with an acyl halide under basic conditions to form a mixed anhydride,
  (c) condensing said mixed anhydride with HX wherein X is an amino acid moiety or a des-carboxy amino acid moiety as defined above, and
  (d) hydrolyzing the product of condensation of step (c) under basic conditions, to provide said composition.

2. The process of claim 1 wherein said blocking reagent is trifluoroacetic anhydride.

3. The process of claim 1 wherein said acid halide is an alkanoyl halide.

4. The process of claim 3 wherein said alkanoyl halide is iso-butylchloroformate.

5. The process of claim 1 wherein the acid employed in step (a) is pteroic acid.

6. The process of claim 5 wherein HX is L-tyrosine methyl ester.

7. The process of claim 5 wherein HX is histamine.

8. The process of claim 5 wherein HX is tyramine.

9. The process of claim 5 wherein HX is 5-hydroxytryptophan methyl ester.

10. The process of claim 5 wherein HX is histidine methyl ester.

11. The process of claim 5 wherein HX is 2(4'-hydroxyphenyl) glycine methyl ester.

* * * * *